US00PP20626P2

(12) United States Plant Patent
Jandrew

(10) Patent No.: US PP20,626 P2
(45) Date of Patent: Jan. 5, 2010

(54) ***PENSTEMON* PLANT NAMED 'PENI VIO09'**

(50) Latin Name: *Penstemon hartwegii benth*
Varietal Denomination: Peni Vio09

(75) Inventor: Jason Jandrew, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,430

(22) Filed: Nov. 10, 2008

(51) Int. Cl.
*A01H 5/00* (2006.01)

(52) U.S. Cl. ..... Plt./465

(58) Field of Classification Search ..... Plt./263, Plt./465

See application file for complete search history.

*Primary Examiner*—Susan B McCormick-Ewoldt
(74) *Attorney, Agent, or Firm*—S. Matthew Edwards

(57) ABSTRACT

A new *Penstemon* plant named 'Peni Vio09,' particularly distinguished by large, purple flowers, upright and medium-compact plants, strong stems, and an earlier flowering habit.

1 Drawing Sheet

Latin name of the genus and species of the plant claimed: *Penstemon hartwegii benth.*

Varietal denomination: 'Peni Vio09'.

BACKGROUND OF THE NEW PLANT

The present invention comprises a new *Penstemon*, botanically known as *Penstemon hartwegii benth*, and hereinafter referred to by the variety name 'Peni Vio09.'

'Peni Vio09' is a product of a planned breeding program. The new cultivar 'Peni Vio09' has large, purple flowers, upright and medium-compact plant, strong stems, and an earlier flowering habit.

'Peni Vio09' originated from a hybridization in a controlled breeding program in Gilroy, Calif. USA. The female parent was a patented hybrid seedling identified as 'Pheni Vio,' U.S. Plant Pat. No. 17,933, with purple color. 'Pheni Vio' has a lighter purple color, a taller habit, and it later to flower than 'Peni Vio09.'

The male parent of 'Peni Vio09' was an unpatented hybrid seedling identified as '104-1' with an apple blossom color. '104-1' has a taller habit, less vigor, and is later to flower than 'Pnei Vio09.'

'Peni Vio09' was selected as one flowering plant within the progeny of the stated cross in April 2005 in a controlled environment in Gilroy, Calif. USA.

The first act of asexual reproduction of 'Peni Vio09' was accomplished when vegetative cuttings taken from the initial selection in April 2006 in a controlled environment in Gilroy, Calif. USA. The pollination took place in July 2005 and the seed sowing in October 2005 all in Gilroy, Calif., USA.

Horticultural examination of plants grown from cuttings of the plant initiated in April 2006 in Gilroy, Calif. USA, and continuing thereafter, has demonstrated that the combination of characteristics as herein disclosed for 'Peni Vio09' are firmly fixed and are retained through successive generations of asexual reproduction.

'Peni Vio09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Peni Vio09' has not been made publicly available more than one year prior to the filing of this application.

DESCRIPTION OF THE DRAWINGS

The accompanying photographic drawing shows typical flower and foliage characteristics of 'Peni Vio09' with colors being as true as possible with an illustration of this type. The photographic drawing shows flowering plants of the new variety and a close-up of the inflorescence.

The flowering plants photo was taken in August 2008 and the plants were growing in field trials in Gilroy, Calif. USA. The close-up photograph was taken in September 2007.

DETAILED BOTANICAL DESCRIPTION

The measurements were taken in April 2008 on plants that were growing in 1 gallon pots in a greenhouse in Gilroy, Calif. USA. Culture of these plants started in about January 2008 in a greenhouse. The plants were about 4 months old.

Color Chart used: Royal Horticultural Society Colour Chart (R.H.S.) 2001

BRIEF SUMMARY OF INVENTION

The following observations, measurements, and comparisons describe plants grown outside in Gilroy, Calif. USA. The following traits have been repeatedly observed and are determined to be basic characteristics of the new variety. The combination of these characteristics distinguishes this *Penstemon* as a new and distinct variety.

TABLE 1

DIFFERENCES BETWEEN THE NEW VARIETY 'PENI VIO09' AND A SIMILAR VARIETY

| | 'Peni Vio09' | 'Pheni Vio' (U.S. Plant Pat. No. 17,933) |
|---|---|---|
| Flower color | Darker purple | Lighter purple |
| Flower response | Earlier | Later |
| Plant habit | More compact/shorter | Less compact/little taller |

Plant:
- *Form, growth and habit*.—Upright and medium-compact plants, strong stems, and good vigor.
- *Plant height*.—29–32 cm.
- *Plant height* (*inflorescence included*).—46–50 cm.
- *Plant width*.—30–35 cm.

Foliage:
- *Arrangement*.—Opposite and decussant.
- *Immature, leaf color, upper surface*.—Closest to RHS 146B.
- *Lower surface*.—Closest to RHS 146B.
- *Mature, leaf color, upper surface*.—Closest to RHS 146A.
- *Lower surface*.—Closest to RHS 146B.
- *Length*.—10.8–12.2 cm.
- *Width*.—2.6–2.7 cm.
- *Shape*.—Lanceolate.
- *Base shape*.—Acuminate.
- *Apex shape*.—Acute.
- *Margin*.—Slightly serrate.
- *Texture*.—Pubescence on both sides.
- *Color of veins, upper and lower surfaces*.—RHS 144C.

Stem:
- *Number of main stems per plant*.—3–4.
- *Number of leaves per stem*.—20–24.
- *Color of stem*.—RHS 144A.
- *Length of stem*.—30–34 cm.
- *Diameter*.—0.4 cm.
- *Length of internodes*.—1.5–2.5 cm.
- *Texture*.—Sparse short pubescence.

Inflorescence:
- *Type*.—On first flowering it appears to be a raceme, then matures to more of a thyrse with short peduncles emerging at the nodes in opposite arrangement, each peduncle bearing 2–4 flowers or buds at various stages of development; the flowers are held somewhat horizontally.
- *Blooming habit*.—Intermittent; removing of spent flowers enhances development of new flowers.
- *Number of inflorescences per plant*.—12–14; early terminal pinching of apices enhances formation of more racemes.
- *Raceme color*.—RHS 144A.
- *Raceme length*.—12–15 cm.
- *Raceme texture*.—Pubescent.
- *Color of peduncle*.—RHS 144B; anthocyanins of RHS N79B to C on the top surface of the peduncle.
- *Length of peduncle*.—0.6–0.7 cm.
- *Diameter of peduncle*.—0.1 cm.
- *Texture*.—Pubescent; glandular hairs.
- *Color of pedicel*.—RHS 144B; anthocyanins of RHS N79B to C on the top surface of the pedicel.
- *Length of pedicel*.—0.5–0.7 cm.
- *Diameter of pedicel*.—0.1 cm.
- *Texture*.—Pubescent to hirsute.

Corolla:
- *Form*.—Zygomorphic and single; funnel-shaped with the petals mainly fused at base, 5 free lobed, opening outward.
- *Fragrance*.—None.
- *Lastingness of individual florets*.—About 6–7 days.
- *Width of floret*.—3.7–4.2 cm.
- *Depth of floret*.—3.8–3.9 cm.
- *Color, upper lobes, upper surface*.—RHS N79B maturing to between RHS N79B and C.
- *Color, upper lobes, lower surface*.—RHS N79C.
- *Length of upper lobes*.—1.1–1.3 cm.
- *Width of upper lobes*.—1.1–1.2 cm.
- *Color, lateral lobes, upper surface*.—Same as upper.
- *Color, lateral lobes, lower surface*.—Same as upper.
- *Length of lateral lobes*.—1.3–1.4 cm.
- *Width of lateral lobes*.—1.5–1.6 cm.
- *Color, lower mid-lobe, upper surface*.—Same as upper.
- *Color, lower mid-lobe, lower surface*.—Same as upper.
- *Length of lower mid-lobe*.—1.1–1.2 cm.
- *Width of lower mid-lobe*.—1.5–1.6 cm.
- *Apex shape*.—Rounded to sometimes slightly obtuse.
- *Margin*.—Entire.
- *Petal texture*.—Papillose and some slight pubescence on both surfaces.
- *Corolla color, inside*.—RHS N155B but whiter.
- *Corolla color, outside*.—RHS N79B to C.
- *Corolla length*.—3.1–3.4 cm.

Bud (just before opening):
- *Color*.—RHS 59A.
- *Length*.—2.7–2.9 cm.
- *Width*.—1.0–1.1 cm.
- *Shape*.—Oblong.
- *Number of sepals*.—5, fused at base.
- *Color of sepals*.—RHS 144B; sometimes with anthocyanins of RHS N79B to C mainly on the margins.
- *Length of sepals*.—0.9–1.1 cm.
- *Width of sepals*.—0.6–0.7 cm.
- *Sepal shape*.—Ovate.
- *Apex shape*.—Acute.
- *Margins*.—Entire.
- *Texture*.—Pubescent; glandular hairs.

Reproductive organs:
- *Pistil*.—1.
- *Style color*.—RHS 67B on the basal one half, with RHS N155B on the upper one half.
- *Style length*.—2.7–3.1 cm.
- *Stigma color*.—RHS 149D.
- *Number of anthers*.—5, 4 of which are fertile.
- *Color of filaments*.—RHS 155D.
- *Length of filaments*.—2.5–2.8 cm.
- *Pollen amount*.—Moderate.
- *Color of pollen*.—RHS 158A.
- *Fertility/seed set*.—Not observed on this hybrid.

Disease/pest resistance: Disease resistance or susceptibility has not been observed on this hybrid.

What is claimed is:

1. A new and distinct variety of *Penstemon* plant named 'Peni Vio09,' substantially as illustrated and described herein.

* * * * *

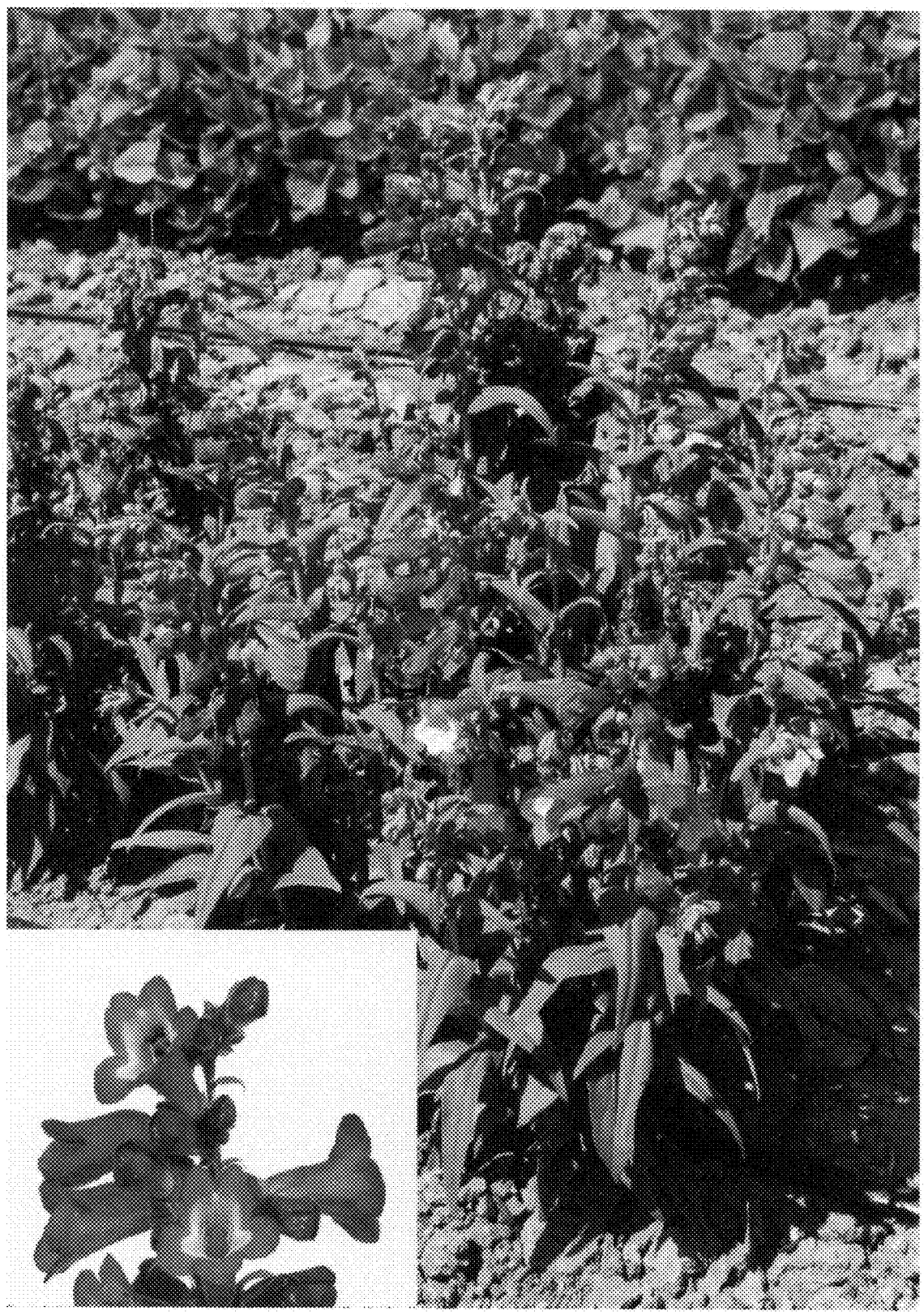

UNITED STATES PATENT AND TRADEMARK OFFICE

CERTIFICATE OF CORRECTION

PATENT NO. : PP 20,626 P2
APPLICATION NO. : 12/291430
DATED : January 5, 2010
INVENTOR(S) : Jandrew It is certified that error appears in the above-identified patent and that said Letters Patent is hereby corrected as shown below:

At column 1, line 25, delete "'Pnei'" and insert therefor --'Peni'--

Signed and Sealed this

Sixteenth Day of February, 2010

David J. Kappos

David J. Kappos
*Director of the United States Patent and Trademark Office*